United States Patent
Feldman et al.

(10) Patent No.: US 12,151,106 B2
(45) Date of Patent: Nov. 26, 2024

(54) ARCHITECTURES FOR AN IMPLANTABLE STIMULATOR DEVICE HAVING A PLURALITY OF ELECTRODE DRIVER INTEGRATED CIRCUITS WITH SHORTED ELECTRODE OUTPUTS

(71) Applicant: Boston Scientific Neuromodulation Corporation, Valencia, CA (US)

(72) Inventors: Emanuel Feldman, Simi Valley, CA (US); Jordi Parramon, Valencia, CA (US); Paul J. Griffith, Moorpark, CA (US); Jess Shi, Northridge, CA (US); Robert Tong, Valencia, CA (US); Goran Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 300 days.

(21) Appl. No.: 17/457,366

(22) Filed: Dec. 2, 2021

(65) Prior Publication Data
US 2022/0088392 A1     Mar. 24, 2022

Related U.S. Application Data

(63) Continuation of application No. 16/443,609, filed on Jun. 17, 2019, now Pat. No. 11,207,521, which is a
(Continued)

(51) Int. Cl.
*A61N 1/36*     (2006.01)
*A61N 1/05*     (2006.01)
*H01L 25/065*   (2023.01)

(52) U.S. Cl.
CPC .......... *A61N 1/36125* (2013.01); *A61N 1/05* (2013.01); *A61N 1/0534* (2013.01);
(Continued)

(58) Field of Classification Search
None
See application file for complete search history.

(56) References Cited

U.S. PATENT DOCUMENTS

| 5,501,703 A | 3/1996 | Holsheimer et al. |
| 5,861,008 A | 1/1999 | Obel et al. |

(Continued)

FOREIGN PATENT DOCUMENTS

| JP | 2010-233846 | 10/2010 |
| WO | 2002/009808 | 2/2002 |

(Continued)

OTHER PUBLICATIONS

International Search Report and Written Opinion regarding application No. PCT/US2013/021703 dated Jul. 5, 2013.

*Primary Examiner* — Michael W Kahelin
(74) *Attorney, Agent, or Firm* — Lewis & Reese, PLLC

(57) ABSTRACT

A new architecture is disclosed for an IPG having a master and slave electrode driver integrated circuits (ICs). The electrode outputs on the ICs are wired together. Each IC can be programmed to provide pulses with different frequencies. Active timing channels in master and slave ICs are programmed to provide the desired pulses, while shadow timing channels in the master and slave are programmed with the timing data from the active timing channels in the other IC so that each chip knows when the other is providing a pulse, so that each chip can disable its recovery circuitry so as not to defeat those pulses. In the event of pulse overlap at a given electrode, the currents provided by each chip will add at the affected electrode. Compliance voltage generation is dictated by an algorithm to find an optimal compliance voltage even during periods when pulses are overlapping.

15 Claims, 13 Drawing Sheets

Related U.S. Application Data continuation of application No. 15/491,492, filed on Apr. 19, 2017, now Pat. No. 10,363,422, which is a continuation of application No. 15/063,072, filed on Mar. 7, 2016, now Pat. No. 9,656,081, which is a continuation of application No. 13/741,116, filed on Jan. 14, 2013, now abandoned.

(60) Provisional application No. 61/586,930, filed on Jan. 16, 2012.

(52) U.S. Cl.
CPC ...... *A61N 1/36171* (2013.01); *H01L 25/0657* (2013.01); *H01L 2224/16225* (2013.01); *H01L 2224/32145* (2013.01); *H01L 2224/32225* (2013.01); *H01L 2224/48227* (2013.01); *H01L 2224/73204* (2013.01); *H01L 2224/73257* (2013.01); *H01L 2224/73265* (2013.01); *H01L 2225/0651* (2013.01); *H01L 2924/15311* (2013.01); *H01L 2924/181* (2013.01)

(56) References Cited

U.S. PATENT DOCUMENTS

| | | | |
|---|---|---|---|
| 5,941,906 A * | 8/1999 | Barreras, Sr | A61N 1/36071 607/66 |
| 6,516,227 B1 | 2/2003 | Meadows et al. | |
| 6,525,986 B2 | 2/2003 | Prutchi et al. | |
| 7,444,181 B2 | 10/2008 | Shi et al. | |
| 7,890,182 B2 | 2/2011 | Parramon et al. | |
| 8,615,306 B2 | 12/2013 | Griffith | |
| 2006/0058588 A1 | 3/2006 | Zdeblick | |
| 2006/0167525 A1 | 7/2006 | King | |
| 2007/0038250 A1 | 2/2007 | He et al. | |
| 2007/0100399 A1 | 5/2007 | Parramon et al. | |
| 2008/0319497 A1 | 12/2008 | Griffith et al. | |
| 2009/0024189 A1 * | 1/2009 | Lee | A61N 1/36017 607/66 |
| 2009/0259278 A1 * | 10/2009 | Torgerson | A61N 1/36125 607/59 |
| 2011/0160810 A1 | 6/2011 | Griffith | |
| 2012/0092031 A1 | 4/2012 | Shi et al. | |
| 2012/0095519 A1 | 4/2012 | Parramon et al. | |
| 2012/0095744 A1 | 4/2012 | Rahman et al. | |
| 2013/0006315 A1 | 1/2013 | Lee | |
| 2013/0023943 A1 | 1/2013 | Parramon et al. | |

FOREIGN PATENT DOCUMENTS

| | | |
|---|---|---|
| WO | 2006/029257 | 3/2006 |
| WO | 2007/117232 | 10/2007 |
| WO | 2008/048321 | 4/2008 |

\* cited by examiner

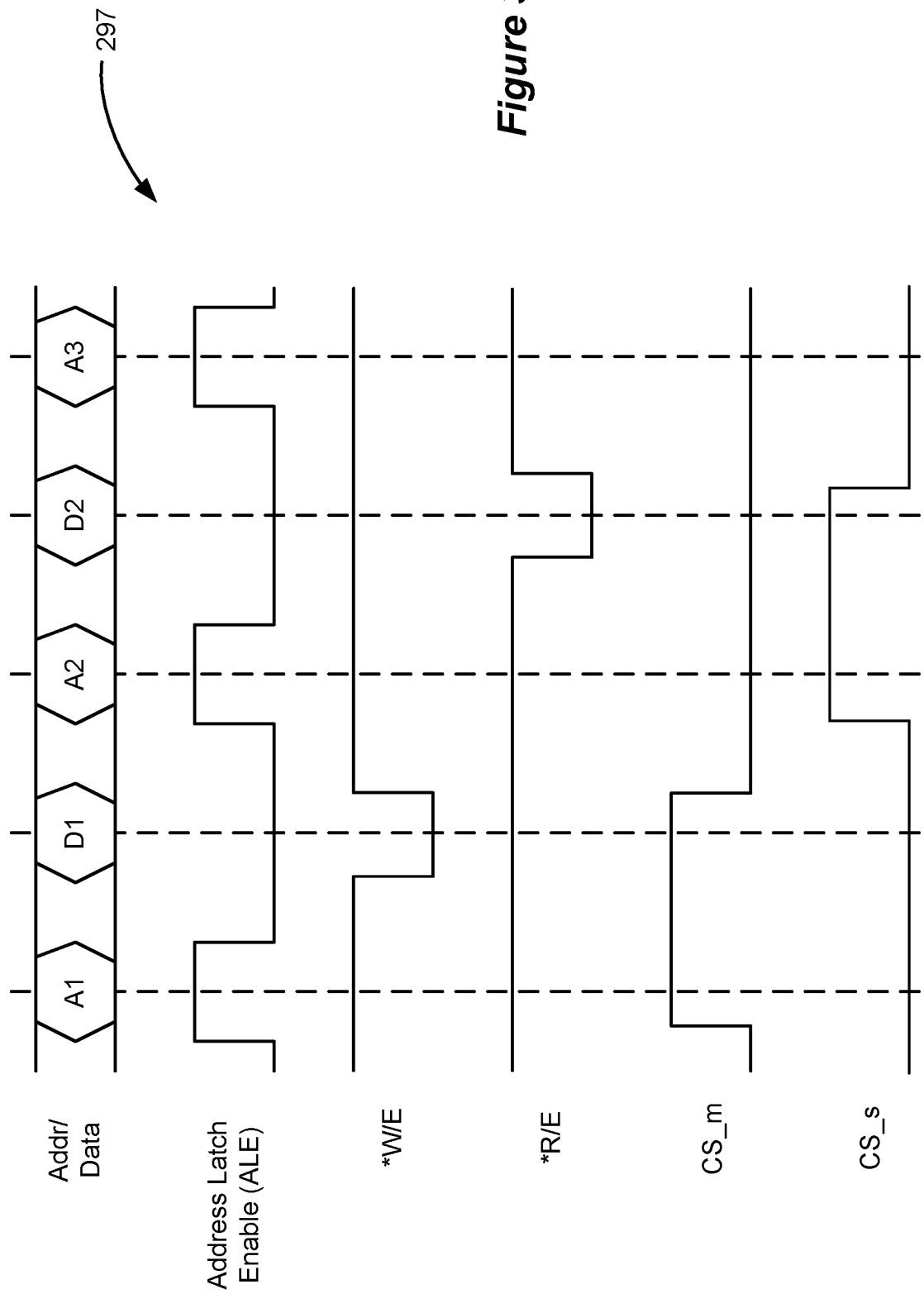

ARCHITECTURES FOR AN IMPLANTABLE STIMULATOR DEVICE HAVING A PLURALITY OF ELECTRODE DRIVER INTEGRATED CIRCUITS WITH SHORTED ELECTRODE OUTPUTS

CROSS-REFERENCE TO RELATED APPLICATIONS

This is a continuation application of U.S. patent application Ser. No. 16/443,609, filed Jun. 17, 2019 (allowed), which is a continuation application of U.S. patent application Ser. No. 15/491,492, filed Apr. 19, 2017 (U.S. Pat. No. 10,363,422), which is a continuation application of U.S. patent application Ser. No. 15/063,072, filed Mar. 7, 2016 (U.S. Pat. No. 9,656,081), which is a continuation application of U.S. patent application Ser. No. 13/741,116, filed Jan. 14, 2013 (now abandoned), which was a non-provisional filing of U.S. Patent Application Ser. No. 61/586,930, filed Jan. 16, 2012. Priority is claimed to these applications, and they are incorporated herein by reference.

FIELD OF THE INVENTION

The present invention relates generally to implantable medical devices, and more particularly to improved architectures for an implantable neurostimulator utilizing a plurality of electrode-driver integrated circuits.

BACKGROUND

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc.

As shown in FIGS. 1A and 1B, an Implantable Pulse Generator (IPG) 100 includes a biocompatible device case 30 formed of a conductive material such as titanium for example. The case 30 typically holds the circuitry and battery 26 necessary for the IPG to function, although IPGs can also be powered via external RF energy and without a battery. The IPG 100 includes one or more electrode arrays (four such arrays 102-105 are shown), each containing several electrodes 106. The electrodes 106 are carried on a flexible body 108, which also houses the individual electrode leads 112-115 coupled to each electrode. In the illustrated embodiment, there are four electrodes 106 on each of arrays 102-105, although the number of arrays and electrodes is application specific and therefore can vary. The conductive case 30 can also comprise an electrode, Ec, as is useful in monopolar stimulation, which will be explained shortly. The arrays 102-105 couple to the IPG 100 using lead connectors 38a-d, which are fixed in a non-conductive header material 36, which can comprise an epoxy for example.

As shown in FIG. 1B, the IPG 100 typically includes an electronic substrate assembly 14 including a printed circuit board (PCB) 16, along with various electronic components 20, such as integrated circuits and capacitors mounted to the PCB 16. Two coils (more generally, antennas) are generally present in the IPG 100: a telemetry coil 13 used to transmit/receive data to/from an external controller; and a charging coil 18 for charging or recharging the IPG's battery 26 using an external charger. The telemetry coil 13 is typically mounted within the header 36 of the IPG 100 as shown, and may be wrapped around a ferrite core 13'. However, the telemetry coil 13 may also appear inside the case 30, such as is disclosed in U.S. Patent Publication 2011/0112610. A discussion of how the IPG 100 communicates with an external controller and an external charger can also be found in the '610 Publication. Further, a single coil could be used for both charging and telemetry functions, as disclosed in U.S. Patent Publication 2010/0069992.

The IPG 100 illustrated in FIG. 1A is particularly (but not exclusively) useful in Deep Brain Stimulation (DBS), as might be useful in the treatment of Parkinson's disease for example. In such an application, the case is 30 typically implanted in the chest or near the base of the skull, with two of the arrays (e.g., 102, and 103) positioned at a desired locations within the right side of the brain, and with the other two arrays (e.g., 104 and 105) positioned within the left side of the brain. These desired locations on each side can comprise the subthalamic nucleus (STN) and the pedunculopontine nucleus (PPN), such that two of the arrays (e.g., 102 and 104) are positioned within the STN, while the other two (e.g., 103 and 105) are positioned within the PPN.

DBS stimulation is typically monopolar, meaning that a given electrode on an array is chosen as the cathode or current sink, with the case electrode (Ec) acting as the anode or current source. Which of the electrodes on a given array will be chosen as the cathode can depend on experimentation—that is, trying of various of the electrodes on the array in succession to see which provides the best therapeutic benefit. Bipolar stimulation can also be used for DBS, in which one non-case electrode acts as the anode and another non-case electrode acts as the cathode, but for simplicity the remainder of this disclosure will focus solely on monopolar stimulation.

Studies suggest that different brain regions respond favorably when stimulated with current pulses of different frequencies. For example, stimulation of the STN provides better therapeutic results when stimulated at higher frequencies (e.g., 130-185 Hz), while stimulation of the PPN provides better therapeutic results when stimulated at lower frequencies (e.g., 25 Hz). Such pulses can generally be interleaved on the two arrays operating at the same frequency on different sides of the brain to prevent interference. For example, 130 Hz pulses provided by arrays 102 and 104 can be interleaved, while 25 Hz pulses provided by arrays 103 and 105 can similarly be interleaved.

However, such interleaving of the pulses does not address the possibility (or probability) that the pulses will overlap at the different frequencies. Consider for example, FIG. 2A, which shows monopolar stimulation of electrode E1 (array 102) at a relatively high frequency (f1), and monopolar stimulation of electrode E7 (array 103) at a relatively low frequency (f2). Also shown are the anodic responses of the case electrode, Ec, which as noted earlier acts as a current source for the cathodic pulses provided on electrodes E1 and E7. Notice at the left side of FIG. 2A that the pulses overlap within the dotted-lined box.

This overlap in pulses can present a problem in the IPG 100, and to understand this, the concept of a timing channel is explained. Each of the pulse trains in FIG. 2A are defined in software in the IPG 100 by timing channels 176, which are shown in further detail in FIG. 2B. As shown, there are four timing channels $176_1$-$176_4$. The timing channels 176 are shown as part of the stimulation circuitry 175 of the IPG 100, but could also reside as logic elsewhere in the IPG 100, such as within its microcontroller 305. Each timing channel 176 is programmed with the basic parameters needed to construct matching anodic and cathodic therapeutic pulses, such as frequency (f), pulse width (pw), amplitude (a), the affected electrodes, and polarity at each of the electrodes (whether an electrode is to act as anode (positive source of current) or a cathode (negative source of current)). Such parameters can be provided to and stored in the timing channel 176 by the microcontroller 305 via a bus 297, with each parameter for each timing channel 176 having its own unique address.

As shown, timing channel $176_1$ (corresponding to array 102) is used to provide the cathodic and anodic pulses respectively at electrode E1 (for example) and Ec (the case electrode) at a particular frequency (f1), pulse width (pw1), and amplitude (a1). Thus, timing channel $176_1$ passes therapeutic current pulses between electrodes Ec and E1, with Ec comprising the current source, and E1 the corresponding current sink. Timing channel $176_2$ (corresponding to array 103) likewise is used to provide cathodic and anodic pulses respectively at electrode E7 (for example) and Ec, but with a different frequency (f2), and with a particular pulse width (pw2), and amplitude (a2). Assuming the type of DBS application described earlier, timing channels $176_1$ and $176_2$ will stimulate different regions on one (e.g., right) side of the brain.

The other timing channels $176_3$ and $176_4$ (corresponding to arrays 104 and 105 respectively) provide pulses of the same frequencies f1 and f2 to electrodes at the other (e.g., left) side of the brain. However, as alluded to earlier, the pulses in these timing channels $176_3$ and $176_4$ can be interleaved with the pulses of the same frequencies in timing channels $176_1$ and $176_2$, and are denoted fx(180°) to designate that fact. Because interleaving pulses of the same frequency prevents overlaps, a particular concern of this disclosure, such interleaved pulses (i.e., timing channels $176_3$ and $176_4$) are largely ignored for simplicity in subsequent discussion.

The information from the timing channels 176 is provided to Digital-to Analog Converter 82 in the IPG 100, which comprises a programmable current source 83 and a programmable current sink 84'. Because the current source 83 and current sink 84' are typically made from P-channel and N-channel devices respectively, they are often referred to as a PDAC and an NDAC to differentiate them. The PDAC 83 sources a current of the amplitude, pulse width, and frequency specified by the timing channel 176, while PDAC 84 provides a matching current sink. A switch matrix 85 can then be used to route the anodic pulses from the PDAC 82 and the cathodic pulses from the NDAC 84 to the electrodes specified in the timing channel 176 issuing the pulse.

As discussed previously with respect to FIG. 2A, when different timing channels are used to define therapeutic pulses of different frequencies, the pulses can overlaps in time. Such overlap was of concern in the prior art, because the PDAC 83 and NDAC 84 could not source and sink two different currents at the same time. This problem suggested two different solutions, neither of which are optimal.

First, arbitration logic 306 (FIG. 2B) could be employed to prevent overlaps from occurring, thus ensuring that the PDAC 83 and NDAC 84 were not called on to produce two different pulses at the same time. (Although shown as appearing in the stimulation circuitry 175, the arbitration logic 306 could appear in the microcontroller 305 as well). Such arbitration logic 306 would identify overlaps, and would tell certain timing channels 176 to hold on issuing pulse information to the DAC 82 to resolve the conflict. However, this scheme affects the otherwise desired frequency of the pulses. For example, and as shown in FIG. 2A, the arbitration logic 306 has operated to shift the pulses provided by timing channel $176_2$ to alleviate the overlap with the pulses in timing channel $176_1$. As such, the frequency of the pulses in timing channel $176_2$ are no longer ideal, and depending on how frequently such overlaps occur, the overall effect of arbitration can significantly vary the frequency of the pulses in this timing channel from their desired value of f2. Unfortunately, the variation of the frequency in this timing channel can reduce the effectiveness of the therapy at the affected region in the brain (i.e., at array 103).

A second solution is to provide the patient with two independent IPGs 100, as shown in FIG. 2C, with one IPG ($100_1$) providing stimulation at the first frequency (f1) to desired regions of the brain (e.g., the STNs via arrays 102 and 104), and the other IPG ($100_2$) providing stimulation at the second frequency to the other regions of the brain (e.g., the PPNs via arrays 103 and 105). Each IPG 100 can be independently programmed, and because each has its own PDAC 83 and NDAC 84 there is no concern about the different frequencies double-scheduling such circuits. The obvious drawback to this approach is the requirement of implanting two IPGs 100 in the patient to provide full therapeutic coverage to all desired brain regions. Two IPGs 100 clearly doubles the cost, doubles patient discomfort, and generally overly complicates therapy for the patient.

A better solution is therefore needed to the aforementioned problems, and is provided by this disclosure.

BRIEF DESCRIPTION OF THE DRAWINGS

FIG. 3A-3D illustrate circuitry and architecture of an improved IPG having two electrode driver ICs in which the electrode outputs are shorted together.

DETAILED DESCRIPTION

Disclosed is a new architecture for an IPG having a master and slave electrode driver integrated circuits (ICs or chips). Uniquely, the electrode outputs on the integrated circuits are wired together. Each integrated circuit can be programmed to provide pulses with different frequencies, as is useful in DBS for example. Active timing channels in each of the master and slave integrated circuits are programmed to provide the desired pulses, while shadow timing channels in the master and slave are programmed at least with the timing data from the active timing channels in the other integrated circuit so that each chip knows when the other is providing a pulse. In this way, each chip can disable its recovery circuitry so as not to defeat those pulses. Arbitration is turned off, so that each chip can provide its pulses at the desired frequency and without rescheduling. In the event of pulse overlap at a given electrode, the currents provided by each chip will add at the affected electrode. Compliance voltage generation for the provision of the pulses is dictated by an algorithm, which seeks to find an optimal compliance voltage for outputting the pulses even during periods when pulses are overlapping.

Figure 3A:
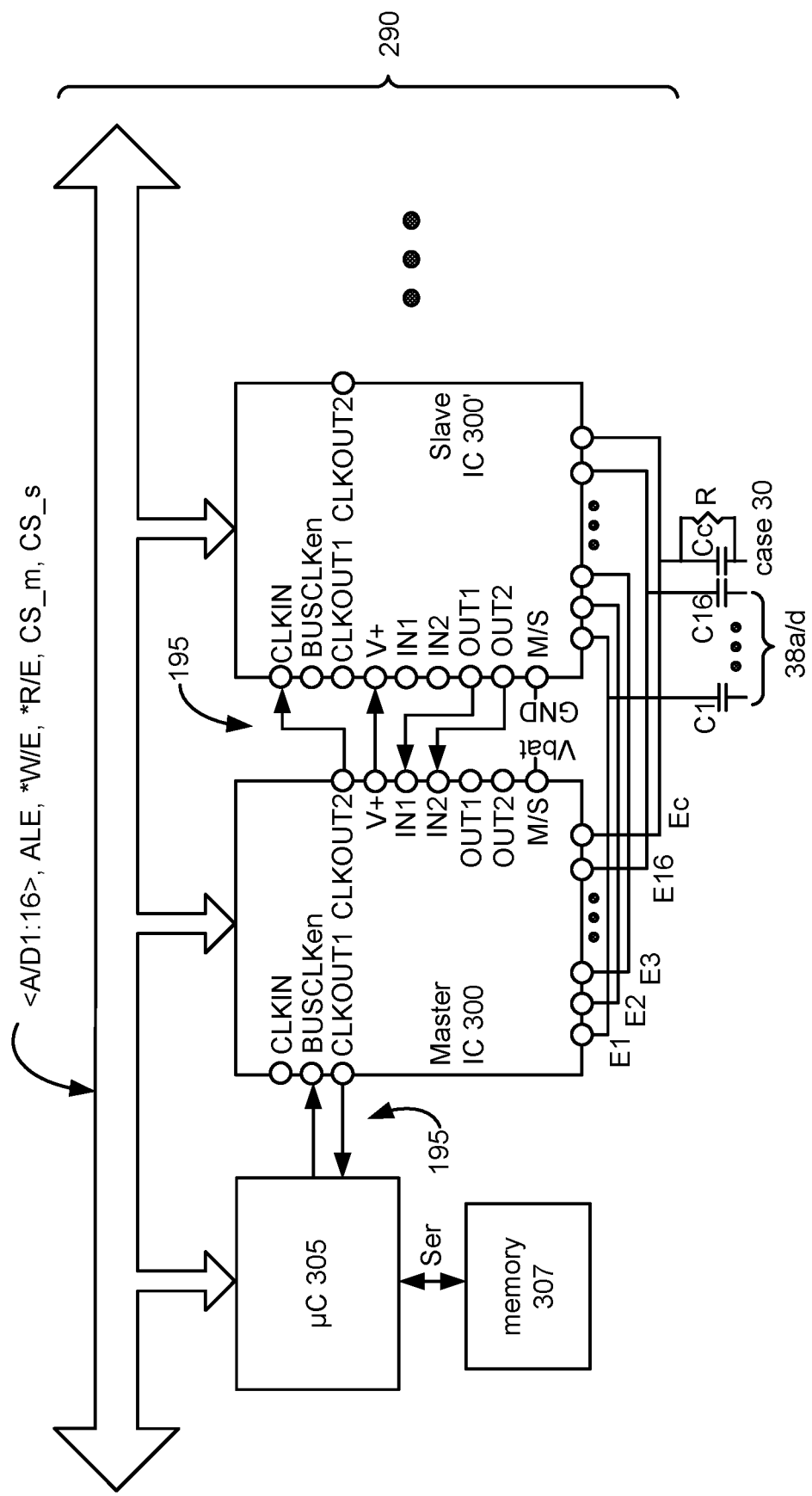

The improved architecture 290 for an IPG is shown first in FIG. 3A. The architecture 290 comprises two electrode driver ICs 300 and 300'. One of the ICs 300 acts as a master, while the other 300' acts as a slave. Both ICs 300 and 300' are connected to a centralized bus 297, upon which communications occur according to a protocol. The signals on the bus 297 are shown in FIG. 3D. The bus 297 comprises time-multiplexed address and data signals (A/Dx); an address latch enable signal (ALE); an active-low write enable signal (*W/E), and an active-low read enable signal (*R/E). These signals allow the protocol to operate using an address-before-data scheme in which an address is followed by pertinent data for that address. To discern between address and data, an address latch enable signal (ALE) is active only upon the issuance of an address, which allows the address to be latched upon the falling edge of the clock. Whether the data corresponding to a particular address is to be written or read on the next falling clock edge depends on the assertion of the write and read enable signals (*W/E; *R/E). Also included in bus 297 are control signals for selecting either of the two chips: CS_m, which comprises a chip select for the master 300, and CS_s, which comprises a chip select for the slave 300'. Using CS_m and CS_s to differentiate between the two ICs 300 and 300' is necessary, because similar circuit blocks in the master 300 and slave 300' ICs can share the same addresses.

Referring again to FIG. 3A, a microcontroller 305 is also connected to the bus 297, which provides for control of functions in the system 290 not handled by various circuit blocks in the ICs 300 and 300', and otherwise generally acts as the system's master controller. For example, bus 297 communications are ultimately controlled by the microcontroller 305, which issues the bus control signals discussed previously (e.g., ALE, W/E*, R/E*, CS_m and CS_s). Microcontroller 305 also controls the issuance of clocks needed for communications on the bus 297 and for internal operations in each of the ICs 300 and 300', as explained in U.S. Patent Application Publication 2012/0095529. The microcontroller 305 can also schedule when the IPG is to listen for telemetry from an external controller for example. Microcontroller 305 connects to a memory (Flash EPROM) chip 307 in the system 290, which can hold the operating software for the system, and which can also act as a free space to log data in the system, e.g., data to be reported to the external controller for analysis and/or feedback to the patient.

In the example shown, each of the ICs 300 and 300' are fabricated identically, even though they are destined to act as either the master or slave in the system 290. Fabricating only a single electrode-driver IC is a great convenience, as the manufacturer does not have to differently fabricate, track, and test separate master and slave ICs for the system 290. Whether any given IC operates as a master or slave depends on how it is connected to the remainder of the system 290, i.e., such chips are bond programmable. As shown in FIG. 3A, each IC has an input, M/S, with the voltage at this input informing each IC whether it is acting as the master 300 or as the slave 300'. This can be accomplished by connecting the M/S input to a particular node on the IPG's PCB, such as Vbat, the voltage of the battery 26 in the IPG, in the case of the master 300, or ground (GND) in the case of the slave 300'. When a given IC understands that it is operating as a slave, it deactivates certain of its circuit blocks, as will be explained later.

Figure 1A:
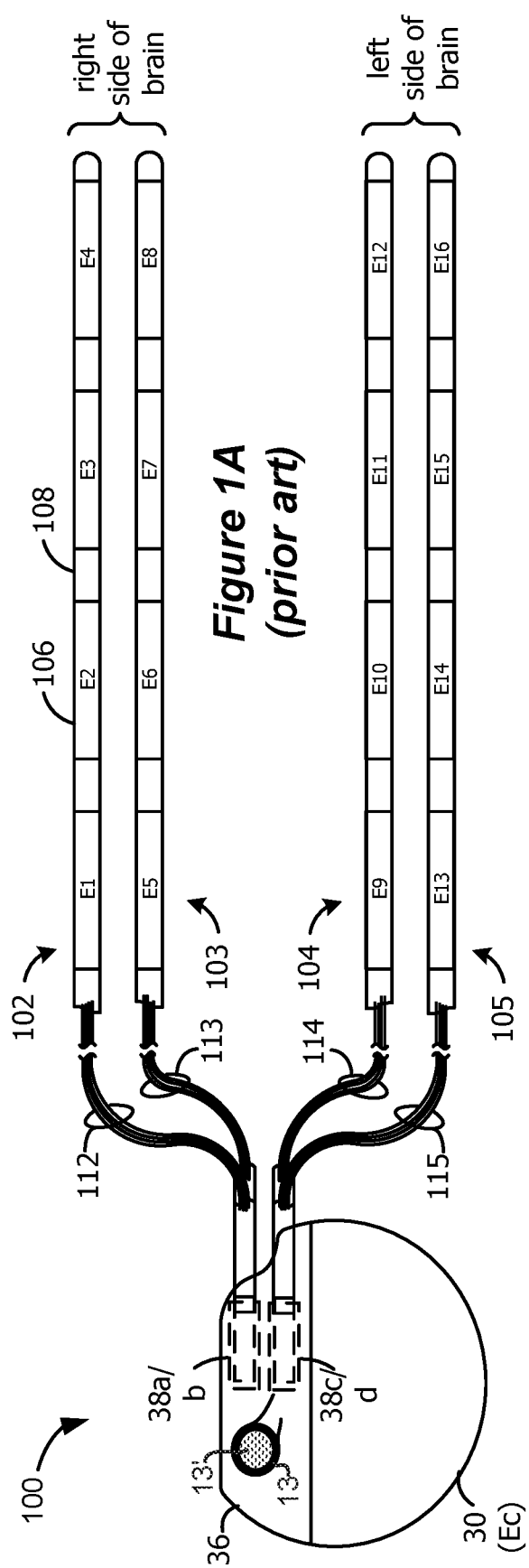
FIGS. 1A-1B show an implantable pulse generator (IPG), and the electrode arrays coupled to the IPG in accordance with the prior art.

Each IC 300 or 300' contains, in this example, 16 electrode outputs, E1-E16, which, like the prior art, are ultimately coupled to the electrodes 106 on arrays 102-105 (FIG. 1A), and one case electrode output, Ec, which is ultimately coupled to the conductive case 30 of the IPG. Such coupling can occur via decoupling capacitors C1-C16 and Cc (FIG. 3C), which improve safety by preventing direct DC current injection to the patient, as is well known. Generally, such decoupling capacitors don't affect stimulation performance. A large 1 M-ohm resistor R can be placed in parallel with the decoupling capacitor for the case, Cc, as shown in FIG. 3A, to allow a small amount of leakage to ensure that the IPG electronics will not float far from the potential of the patient's tissue.

Figure 1B:
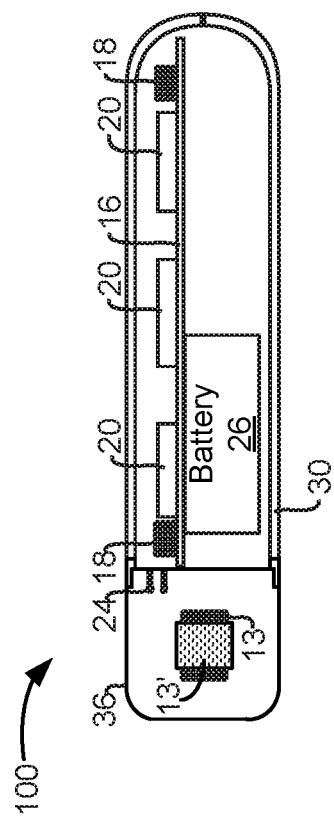
Figure 4:
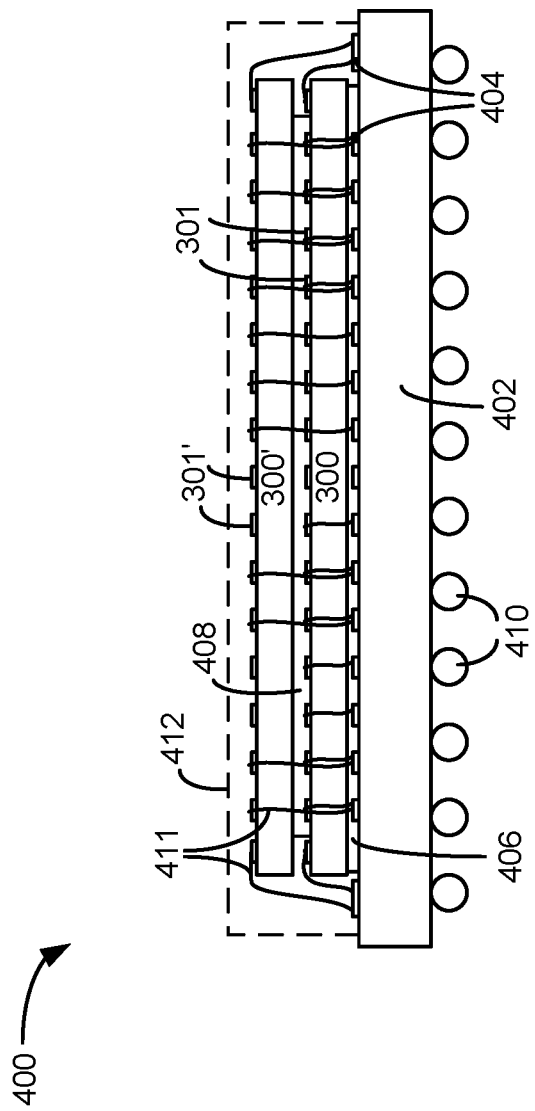
FIG. 4 illustrates an optional BGA package for housing the two electrode driver ICs of the improved IPG.

Unique to system 290, each of the electrode outputs of the master and slave ICs 300 and 300' are shorted together off chip, e.g., on the PCB 16 (FIG. 1B) of the IPG or by wire bonding as will be discussed subsequently in the alternative packaging configuration of FIG. 4. As such, in this architecture 290, even though 32 electrodes outputs (34 including the case 30) are provided by the ICs 300 and 300', they together will support activation of only 16 electrodes on the IPG (17 including the case 30).

Figure 3B:
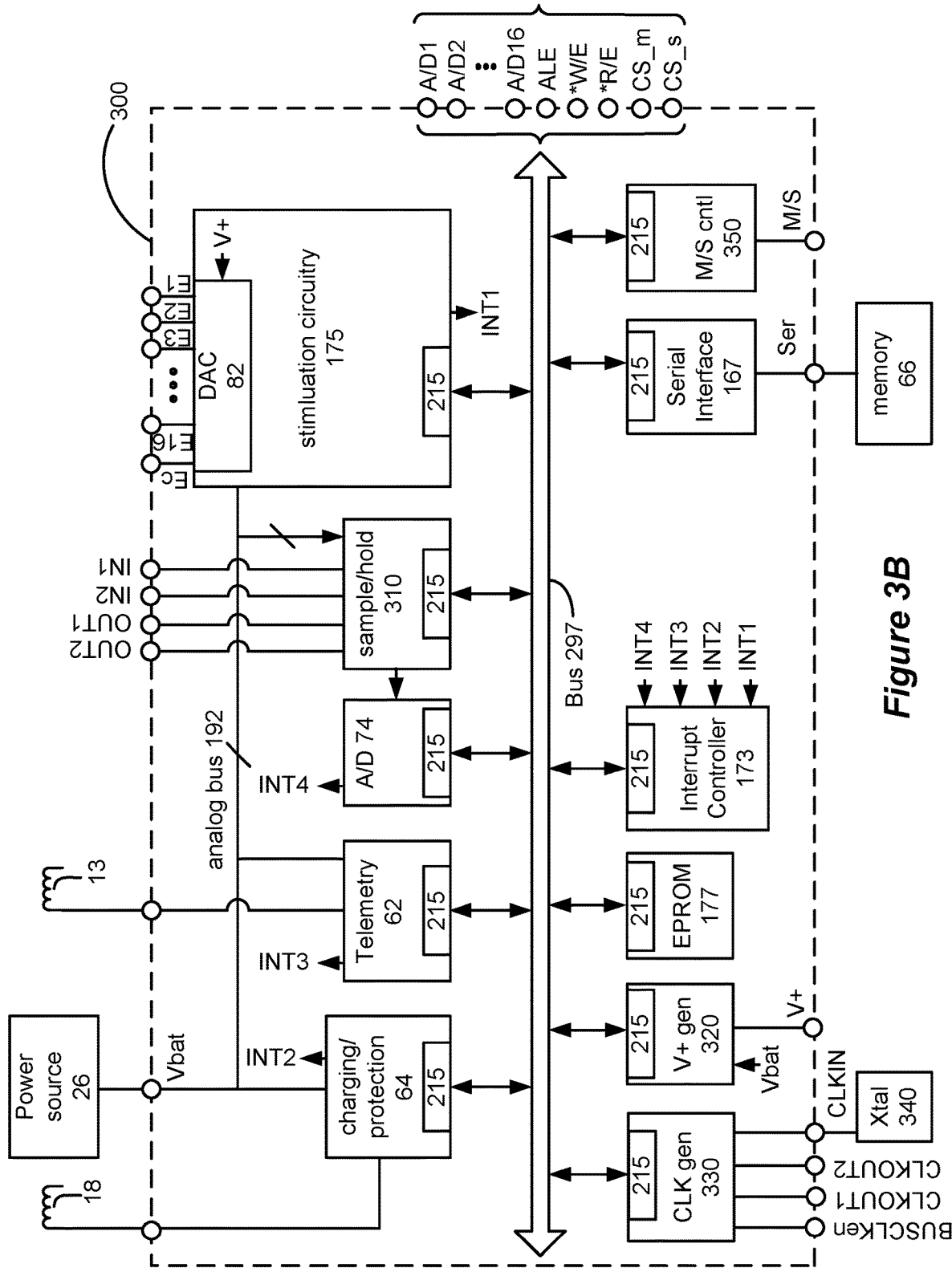

FIG. 3B shows the circuit blocks in either of the identical master 300 or slave 300' ICs. Each circuit block includes bus interface circuitry 215 adherent with the protocol discussed earlier, and each is associated with an address (or a range of addresses) to organize communications on the bus 297.

Each of the circuit blocks performs standard functions in an IPG, and are discussed further in the '529 Publication referenced above. Telemetry block 62 couples to the IPG telemetry coil 13 (FIG. 1B), and includes transceiver circuitry for communicating with an external controller. The charging/protection block 64 couples to the IPG charging coil 18 (FIG. 1B), and contains circuitry for rectifying power received from an external charger, and for charging battery 26 in a controlled fashion.

Stimulation circuit block 175, introduced earlier in the Background, is coupled to the electrode outputs, and includes timing channels and DAC circuitry 82 for defining and outputting pulses of a specified therapy. How this occurs will be discussed subsequently with reference to FIGS. 5A and 5B.

Sample and hold circuitry block 310 contains circuitry for sampling and holding various analog voltages provided by an analog bus 192, including the electrode voltages, the battery voltage, and other analog signals of interest, and is explained in detail in U.S. Pat. No. 9,061,140. Once sample and hold block 310 has operated to resolve a particular voltage, it can be sent to the A/D block 74, where it is digitized and disseminated via the communication bus 297 to wherever in the system 290 it is needed for analysis. Signals IN1, IN2, OUT1 and OUT2 can be used to route various analog signals between the two ICs 300 and 300', as explained in U.S. Pat. No. 8,768,453. Note that because it handles both analog and digital signals, IC 300 comprises a mixed mode chip.

V+ generator block 320 generates a compliance voltage, V+, which is used by the current sources (DAC 82) in the stimulation circuitry block 175. It does so by voltage boosting the battery voltage, Vbat, to an appropriate V+ voltage used to power the current sources (i.e., DACs 82) to an optimal level. This optimal level for V+ can be deduced in part by monitoring the electrode voltages during stimulation, as will be discussed subsequently with reference to FIGS. 6A and 6B.

Clock generator 330 generates the communications clocks used by the communications protocol on the bus 297. While the master IC 300 can derive and provide a clock to the slave IC 300' at its clock input, CLKIN (FIG. 3A), as explained in detail in the '529 Publication, simpler clocking mechanisms could also be used. For example, a system clock could be provided to the clock inputs, CLKIN, of both ICs 300 and 300'.

Figure 3C:
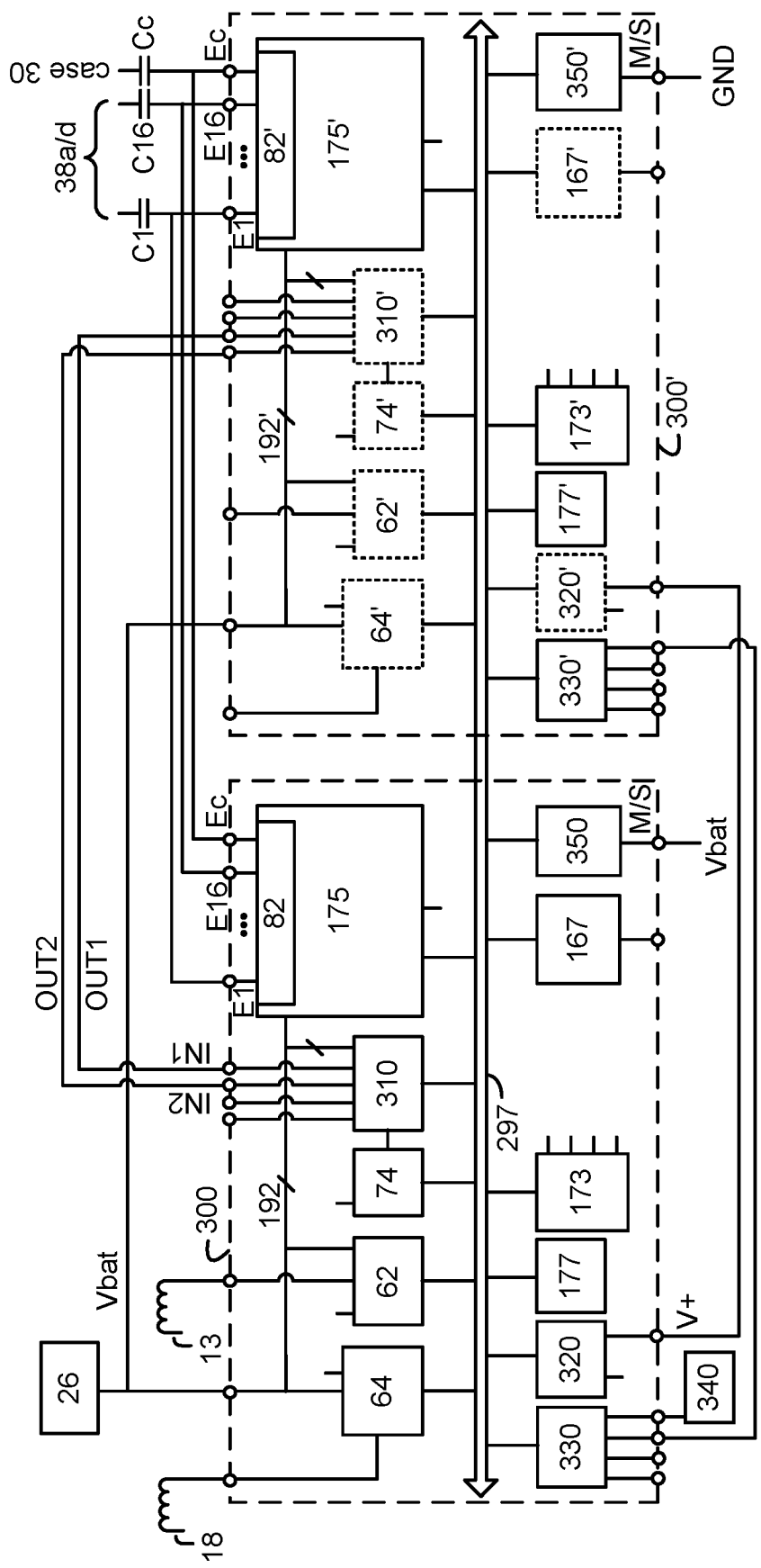

Master/slave controller 350 receives the hardwired M/S input mentioned earlier, and interprets that input to inform the IC whether it is operating and a slave or master, and this is illustrated further in FIG. 3C. In FIG. 3C, the master and slave 300 and 300' are shown as connected with corresponding circuit blocks in the slave IC 300' denoted by a prime symbol. In the slave IC 300' the master/slave controller 350' interprets the grounded input, and informs certain other circuit blocks that they are to be disabled in favor of use of those same circuit blocks in the master IC 300. Specifically, the charging/protection block 64', telemetry block 62' A/D block 74', sample and hold block 310', V+ generator 320', and serial interface block 167 are all disabled in the slave IC 300', and are shown in dotted lines to illustrate that fact. Disabling of each of these circuit blocks can occur in accordance with the state machines operating at each block upon receipt of information from the master/slave controller 350, and such disabling can be affected by disabling the bus drivers and bus receivers operating in the interface circuitry 215 in the affected blocks (FIG. 3B). Still operative in the slave IC 300' are the stimulation circuitry block 175' coupled to the electrodes, and the master/slave controller 350' itself, and other blocks of lesser importance.

Referring again to FIG. 3B, interrupt controller block 173 receives various interrupts from other circuit blocks, which can be sent via bus 297 to the microcontroller 305.

The master and slave ICs 300 and 300' in system 290 could each be individually packaged and connected to the IPG's PCB 16 (FIG. 1B), with appropriate connections between them (such as the connected electrode outputs) being made on the PCB itself. FIG. 4 though shows another way to accommodate both ICs 300 and 300' in one Ball Grid Array (BGA) package 400. As shown, one of the ICs (master IC 300 as shown) can be attached to an interposer 402 by a die attach material 406. The surface of the interposer 402 contains contacts 404, which connect through the interposer 402 to balls 410 on the bottom of the substrate. Ultimately these balls 410 can be surface mounted to the IPG's PCB 16, as is well known. The other IC (slave IC 300' as shown) is then vertically stacked on top and separated from the bottom IC by a separator 408. The separator 408 is sized so that the bond pads 301 of the bottom IC remain exposed, and, like the bond pads 301' on the top IC, can be wire bonded 411 to the contacts 404 on the interposer 402. Thus, nodes common to both ICs—like the electrode outputs—can be shorted within the BGA package 400 at the contacts 404. Other inputs or outputs on the ICs requiring unique connections—like the M/S inputs—would not be shorted, and instead the appropriate bond pads 301 or 301' would be individually wirebonded to an appropriate contact 404 on the interposer 402, or would not be wirebonded at all if no connection is required. Once wirebonded, the assembly can be encapsulated 412 using a cap or mold-injected plastic to complete manufacture of the BGA package 400.

Packaging of the master and slave ICs 300 and 300' in a single BGA package 400 is advantageous because it reduces size and cost, improves reliability, and because it can fit within existing single-IC packages. In other words, BGA package 400 does not increase the "footprint" of the electrode driver circuitry on the IPG's PCB 16 compared to the use of one IC alone, and thus the BGA package 400 can be used as a "drop in" component in legacy IPGs that might have used only a single electrode driver IC. This allows such legacy IPGs to benefit from the improved functionality of architecture 290, which improvements are now discussed.

Figure 2A:
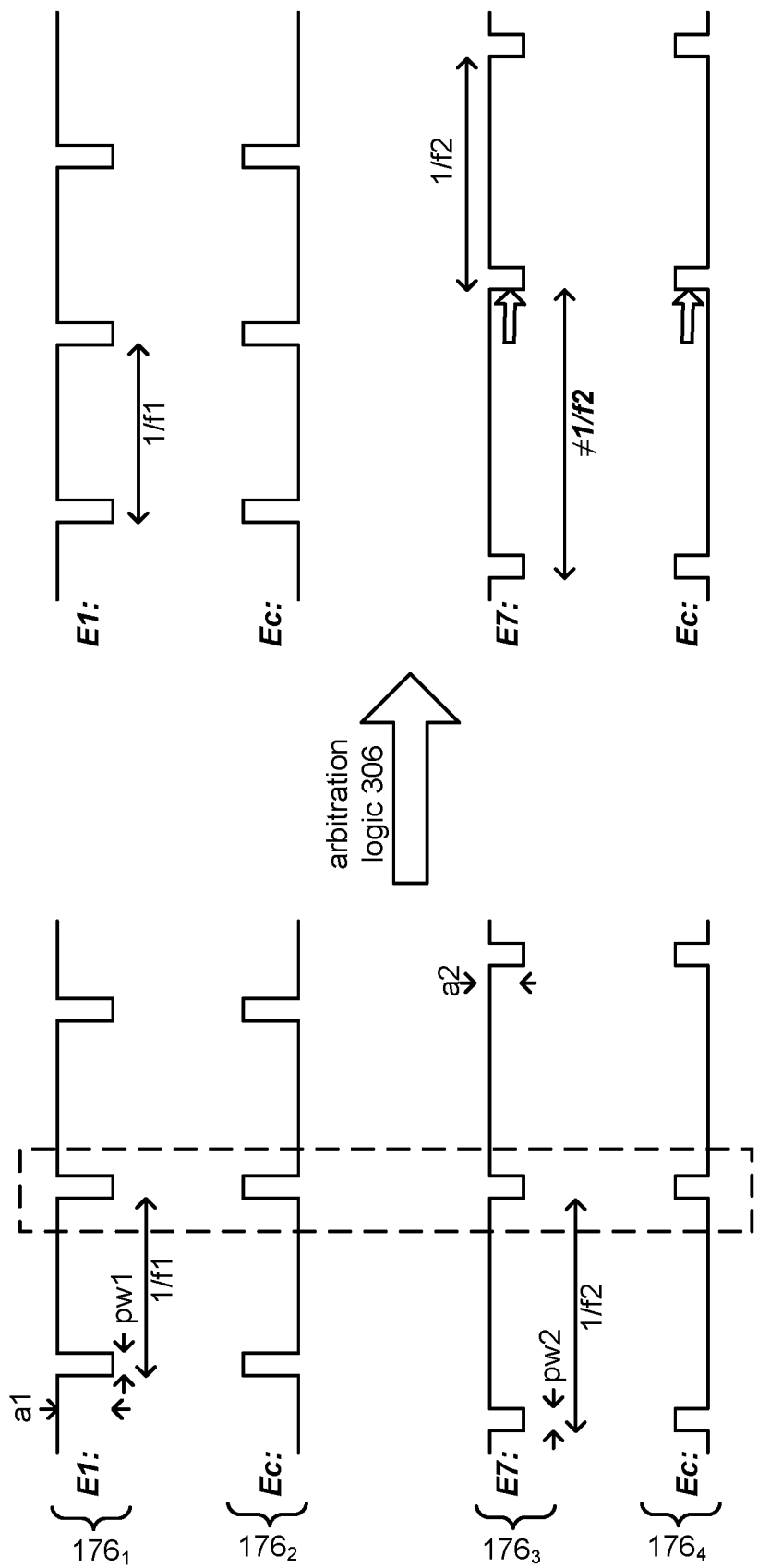
FIG. 2A-2C illustrates aspects of the circuitry of the prior art IPG, and illustrates problems and prior art solutions with respect to overlapping pulses of differing frequencies.
Figure 2B:
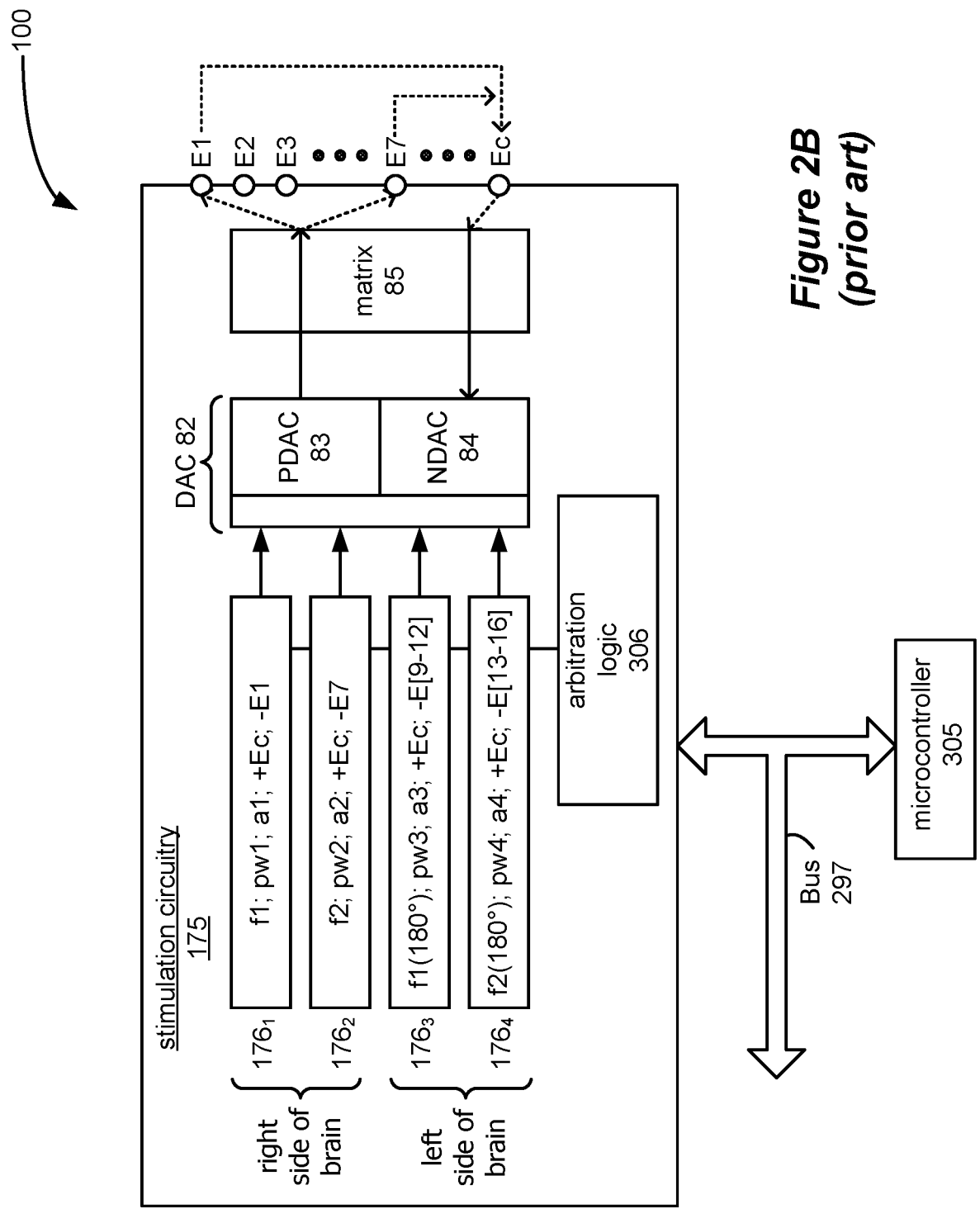
Figure 2C:
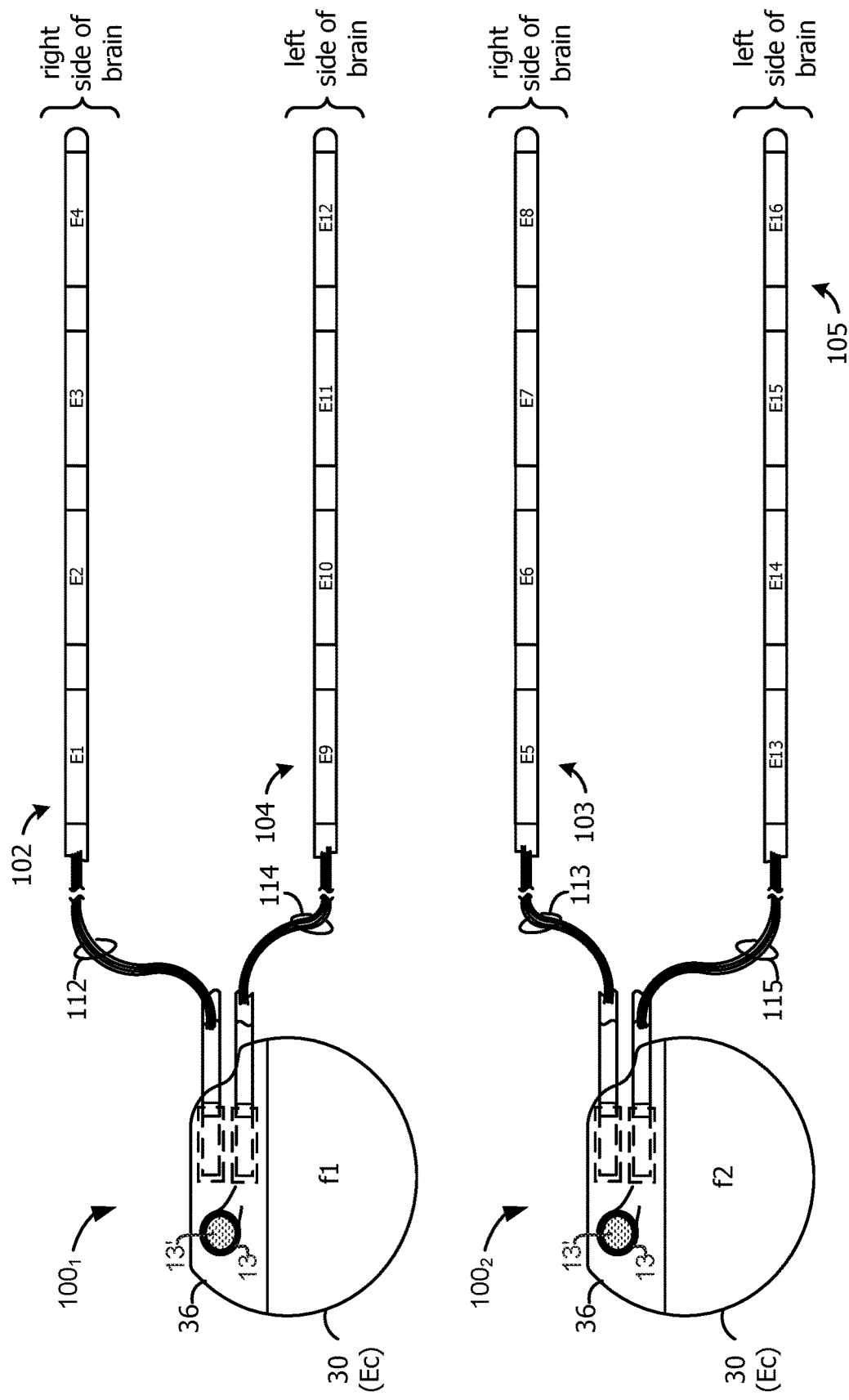
Figure 5A:
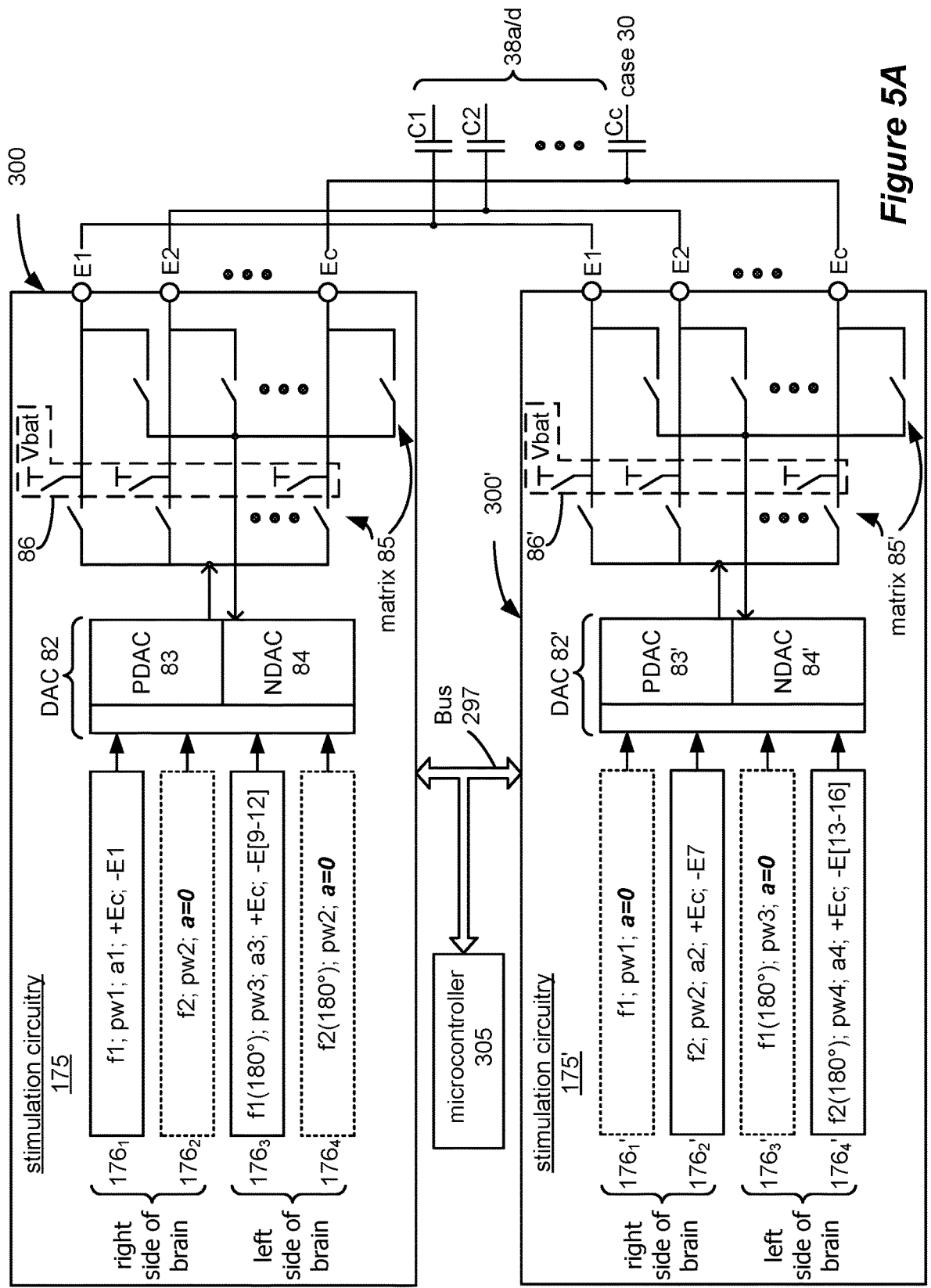
FIGS. 5A and 5B illustrate how the improved IPG operates to provide pulses of differing frequencies despite overlaps in the pulses.

FIG. 5A shows the stimulation circuitry 175 and 175' of both the master and slave ICs 300 and 300'. As before (FIG. 2B), both ICs contain four timing channels 176, each for controlling a particular array 102-105 (FIG. 1A) implanted at a particular region of the brain. As before, the timing channels 176 define anodic and cathodic pulses, and in each IC these pulses are of a different frequency, as is desirable for DBS. Specifically, active timing channel $176_1$ in the master IC 300 is used to provide therapeutic pulses to array 102 at the right side of the brain, e.g., between Ec and E1, at frequency f1, pulse width pw1, and amplitude a1 to stay with the same example discussed in the background. Likewise, active timing channel $176_2$' in the slave IC 300' provides therapeutic pulses to array 103 at the right side of the brain, e.g., between Ec and E7, at frequency f2, pulse width pw2, and amplitude a2.

Figure 5B:
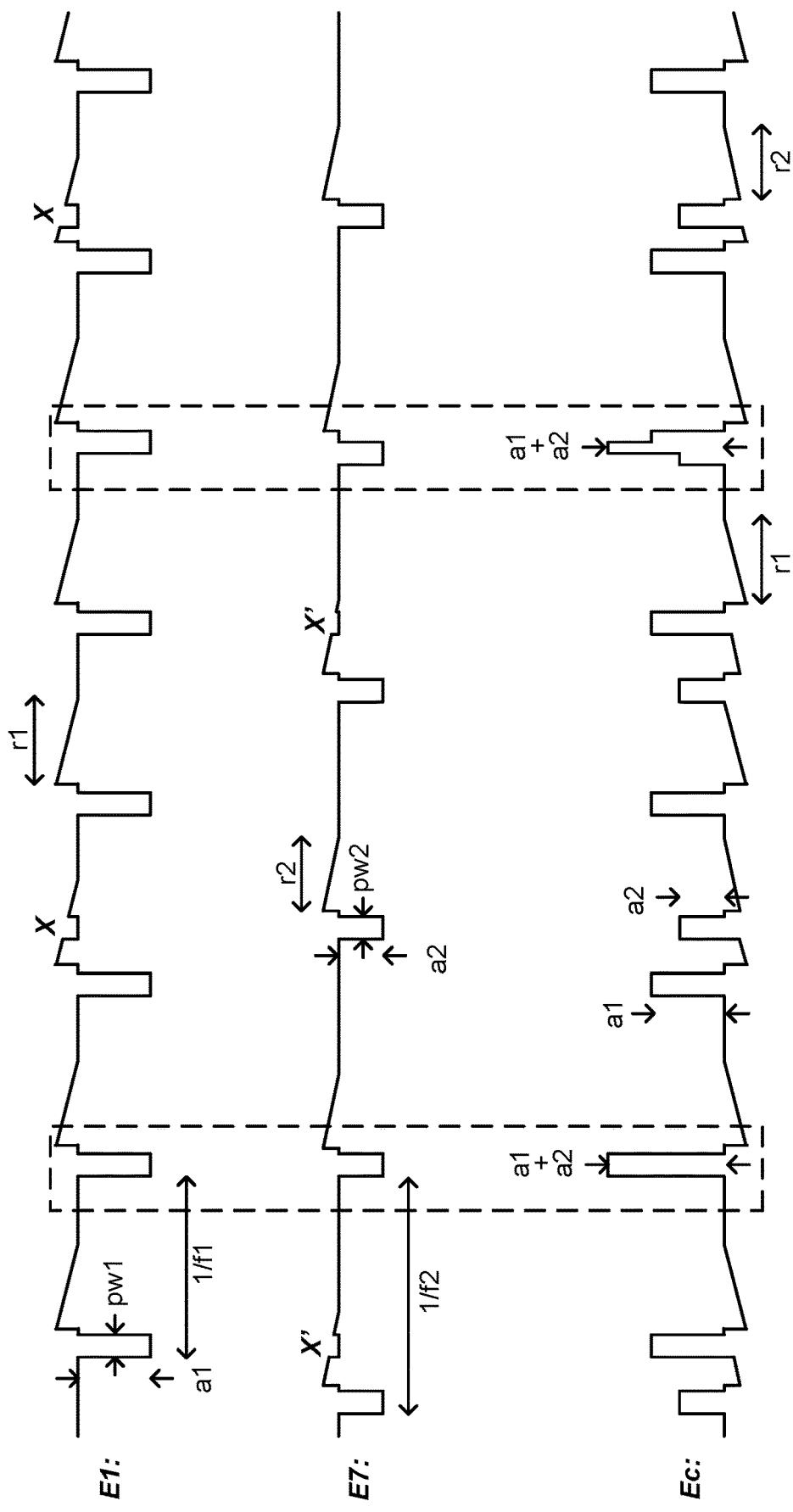

The pulses produced by programming the timing channels in this way are shown in FIG. 5B, and aspects of that Figure are discussed in the following paragraphs. Notice that the cathodic pulses are issued at electrodes E1 and E7 at the desired frequencies (f1 and f2 respectively) without delays or rescheduling. Thus, in distinction to the prior art, desired therapy at set different frequencies is achieved without arbitration and using a single IPG, which is particularly useful in DBS therapy. The case electrode Ec common to both timing channels $176_1$ and $176_2$' reflects the anodic superposition of the cathodic pulses at E1 and E7, which is discussed further below.

Other non-active timing channels in each of ICs 300 and 300' are referred to as shadow timing channels, and are shown in dotted lines in FIG. 5A to denote that fact. These shadow timing channels are programmed with the timing information of the active timing channels in the other IC. Thus, shadow timing channel $176_2$ in the master IC 300 is programmed with the same frequency (f2) and pulse width (pw2) as the active timing channels $176_2$' in the slave IC 300'. Likewise, shadow timing channel $176_1$' in the slave IC 300' is programmed with the same frequency (f1) and pulse width (pw1) as the active timing channel $176_1$ in the master IC 300. As such, each IC knows when the other IC is scheduled to issue pulses.

It is not necessary in this example however that each IC knows the amplitude of the other IC's pulses, nor the electrodes that will receive those pulses, although such additional information can be programmed into the timing channels 176 if desirable or useful. Thus, it can be seen in FIG. 5A that the amplitudes in the shadow timing channels $176_2$ and $176_1$' are set to zero (or to don't care values), and that the electrodes stimulated in the other IC are not reported (or again, set to don't care values). Programming of the timing channels 176 and 176' as before can occur via the bus 297, with signals CS_m and CS_s (FIG. 3D) allowing the timing channels at each of the ICs 300 and 300' to be separately addressed.

Also shown in FIG. 5A are the active timing channels $176_3$ and $176_4$' for providing interleaved pulses to the other side of the brain (i.e., to arrays 104 and 105 on the left side), and their respective shadow timing channels $176_3'$ and $176_4$. Similar to channels $176_3$ and $176_4$ as discussed in the Background, the pulses provided by these active timing channels $176_3$ and $176_4'$ are interleaved with the pulses of the same frequencies in timing channels $176_1$ and $176_2'$, and are denoted fx(180°) to designate that fact. Because interleaving pulses of the same frequency prevents overlaps, a particular concern of this disclosure, such interleaved pulses (i.e., timing channels $176_3$, $176_4$, $176_3'$, $176_4'$) are largely ignored for simplicity in subsequent discussion. While useful in an actual DBS application, timing channels $176_3$, $176_4$, $176_3'$, $176_4'$ are not required in all useful embodiments of an IPG employing architecture 290.

It is important that each IC understand the pulse timing of the other IC for practical reasons, including charge recovery. Charge recovery is well known in the IPG art, but is briefly explained. It is desirable in IPG technology that charge not build up in the tissue being stimulated, and as such it is desired that current injected from a given anode be entirely received at given an cathode. However, perfect charge recovery is difficult to achieve given the use of decoupling capacitors C1-C16 and Cc, and other capacitances that may be inherent in the tissue being stimulated.

Therefore, after each pulse, the IPG preferably performs charge recovery for a duration before the issuance of a next pulse. These charge recovery periods are shown in FIG. 5B as "r1" for active timing channel $176_1$ in master IC 300 (which stimulates E1), and "r2" for active timing channel $176_2'$ in the slave IC 300' (which stimulates E7). During these charge recovery periods, capacitances between the electrodes are shorted together to drain any remaining charge, which is accomplished by charge recovery switches 86 and 86' shown in FIG. 5A. (These recovery switches 86 and 86' are shown intermixed with the switching matrix 85 and 85' used to route the currents provided by the PDAC 83 and NDAC 84 to any desired electrode). As shown, the recovery switches 86 and 86' short each of the electrodes to the battery 26 voltage, Vbat, which effectively shorts the electrodes to each other, and thus shorts capacitances between them to recover any remaining charge. Shorting to Vbat is desired to prevent any electrode from going above the compliance voltage (V+) or below ground (GND). However, the recovery switches could short the electrodes to any desired potential in the IPG.

The shadow timing channels in each of the ICs assist with ensuring that charge recovery at one of the ICs 300 or 300' does not adversely affect the issuance of pulses at the other of the ICs. Specifically, because the shadow timing channels inform each IC when the other IC is issuing pulses, each IC can suspend charge recovery by opening its recovery switches. Suspending charge recovery in this fashion can be seen at the artifacts X and X' in FIG. 5B. Artifacts X at electrode E1 (stimulated by the master IC 300) occur when E7 (stimulated by the slave IC 300') is issuing a pulse (per timing channel $176_2'$). Thus, the master IC 300 has opened its recovery switches 86 during X to prevent pulses issued at electrodes E7/Ec by the slave IC 300' from being shorted to Vbat. Likewise, artifacts X' at electrode E7 (stimulated by the slave IC 300') occur when E1 (stimulated by the master IC 300) is issuing a pulse (per timing channel $176_1$). Thus, the slave IC 300 has opened its recovery switches 86' during X' to prevent pulses issued at electrodes E1/Ec by the master IC 300' from being shorted to Vbat. If no recovery period is currently underway at one IC while the other is issuing pulses, the recovery switches at the one IC would be opened anyway, and thus the risk of shorting the other IC's pulses is moot.

Also noted earlier, the case electrode Ec in FIG. 5B reflects the anodic superposition of the cathodic pulses at E1 and E7. Thus, where anodic pulses from Ec in the two active timing channels on the master IC ($176_1$) and the slave IC ($176_2'$) overlap, their currents are added (a1+a2). Two such incidents of overlap are shown in FIG. 5B, with the left most showing a complete overlap, and the right most showing a partial overlap. This results in an occasional pulse which is not otherwise not therapeutically called for; no timing channel is called upon to supply a pulse of amplitude a1+a2 for example. However, it is not believed that this occasional superposition of currents will negatively affect therapy. Moreover, it is believed that such deviation from specified therapy is overshadowed by the more significant benefit of constant dual frequency pulses in a single IPG.

A remaining consideration to understand in the improved architecture 290 relates to setting of the compliance voltage, V+, which is discussed with reference to FIGS. 6A and 6B. The compliance voltage V+ comprises the power supply voltage used by the DAC circuitry that issues the pulses. As noted earlier, the compliance voltage is generated by V+ generator 320 in the master IC 300, and is sent to the DAC circuitry 82 in the master IC 300, and to the DAC circuitry 82' in the slave IC 300' via an interconnect between the two ICs (see FIG. 3C). V+ is generated by boosting the battery voltage, Vbat, and it is desired that V+ be set to an optimal level: if too low, the electrodes will not be able to issue pulses of the desired amplitudes; if too high, battery power is unnecessarily wasted. See U.S. Pat. No. 7,444,181, discussing this issue in further detail.

In the improved system, V+ is set using an algorithm 500, which is programmed into the microcontroller 305. By way of introduction, the goal of V+ algorithm 500 is to set V+ at a level sufficient to handle the worst case during when the issued pulses will need the most power. In the disclosed example, such worst case will occur when the pulses are overlapping in time, such as occurred in the dotted-lined boxes of FIG. 5B. During such periods of overlap, both of the PDACs 83 and 83' and the DACs 84 and 84' in the master and slave ICs 300 and 300' will be operating. If V+ is set to handle this worst case scenario, it should be high enough (in fact, from an efficiency standpoint, too high) to handle less power-intensive periods when pulses are not overlapping at the two ICs.

Figure 6A:
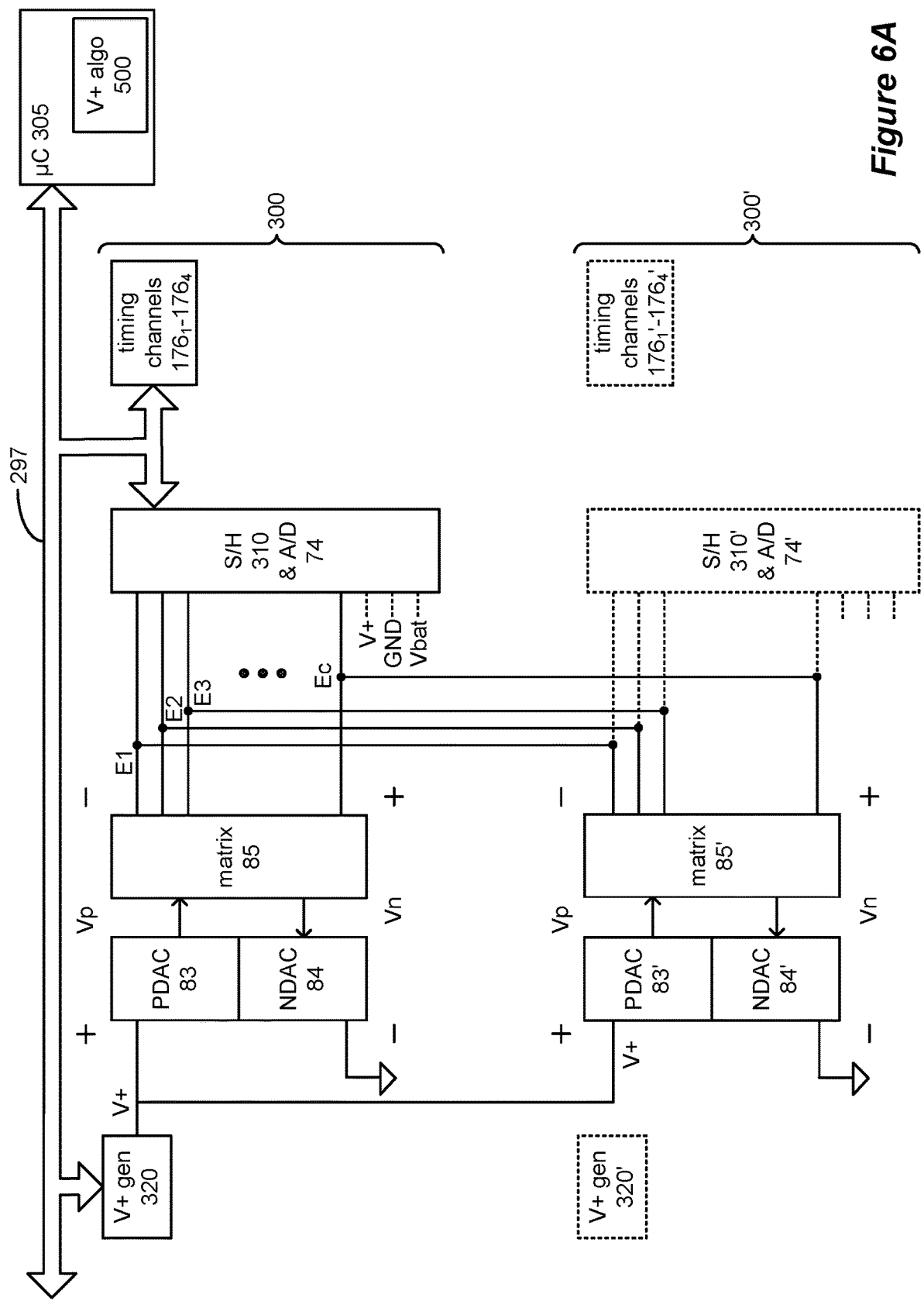
FIGS. 6A and 6B illustrate circuitry and an algorithm for setting a compliance voltage for the DACs in the improved IPG.

FIG. 6A shows the circuitry that is implicated in both ICs 300 and 300' in assessing and setting V+ according to the algorithm 500. Not already discussed in detail, but shown in FIG. 6A, is sample and hold circuitry 310 and an A/D converter block 74. Such circuitry is inactive in the slave IC 300, as previously noted. The electrode voltages, and certain reference potentials, are received by the sample and hold block 310, where they can be stabilized and subtracted. Details of the sample and hold circuitry 310 can be found in U.S. Pat. No. 9,061,140. This patent is incorporated herein by reference, and thus is not discussed in full detail.

As important here, the sample and hold block 310 measures Vp, the voltage drop across the PDACs 83 and 83', and Vn, the voltage drop across the NDAC 82 and 82'. (Voltage drops across the switch matrices 85 and 85' are also included in these measurements, but are relatively small). During operation of the V+ algorithm 500, these parameters Vp and Vn are measured at the affected electrodes during the issuance of pulses from either the master or slave IC 300 or 300'. The shadow timing channels in the master IC 300 (FIG.

5A; $176_2$ and $176_4$) are once again useful in this regard, because they inform the sample and hold circuitry 310 in the master IC 300 of the timing of the pulses in the slave IC 300', which would otherwise be unknown to the master. In short, the timing channels 176 inform the sample and hold circuitry 310 when pulses are being issued, and thus when the Vp and Vn measurements should be made. The sample and hold circuitry 310 further comprises a multiplexer (mux) for choosing the appropriate electrode and reference voltages, as disclosed in the above-incorporated '140 patent.

For example, when a cathodic pulse is being issued at E1, E1 and ground (GND) would be selected by the mux in the sample and hold circuitry 310 and subtracted to determine Vn. By contrast, the corresponding anode Ec and V+ would be selected and subtracted to determine Vp. Which electrodes are being stimulated, and are thus chosen by the sample and hold circuitry 310, can be determined via bus 297, and read from either the timing channels 176 (if programmed for the slave) or directly from the microcontroller 305. Once measured, the Vp and Vn voltages are digitized by A/D block 74, and sent via bus 297 to the microcontroller 305 where they can be considered by the V+ algorithm 500.

Note that the particular implementation of the sample and hold circuitry 310 incorporated herein cannot measure Vp and Vn at the same time. Thus, sample and hold circuitry 310 might sequentially measure Vp for Ec (but not Vn for E1); then Vn for E7 (but not Vp for Ec); then Vn for E1 (but not Vp for Ec); etc. In short, it is not important to V+ algorithm 500 to measure every single pulse, or to measure anodic and cathodic pulses concurrently, although this is possible in different implementations.

What is important is to make sure that the worst case scenario, typically overlapping, is adequately measured. As such, both Vp and Vn must at least occasionally be measured during periods of overlap to assess whether the compliance voltage V+ is inadequate and must be raised, or sufficient but capable of being lowered to save power.

Figure 6B:
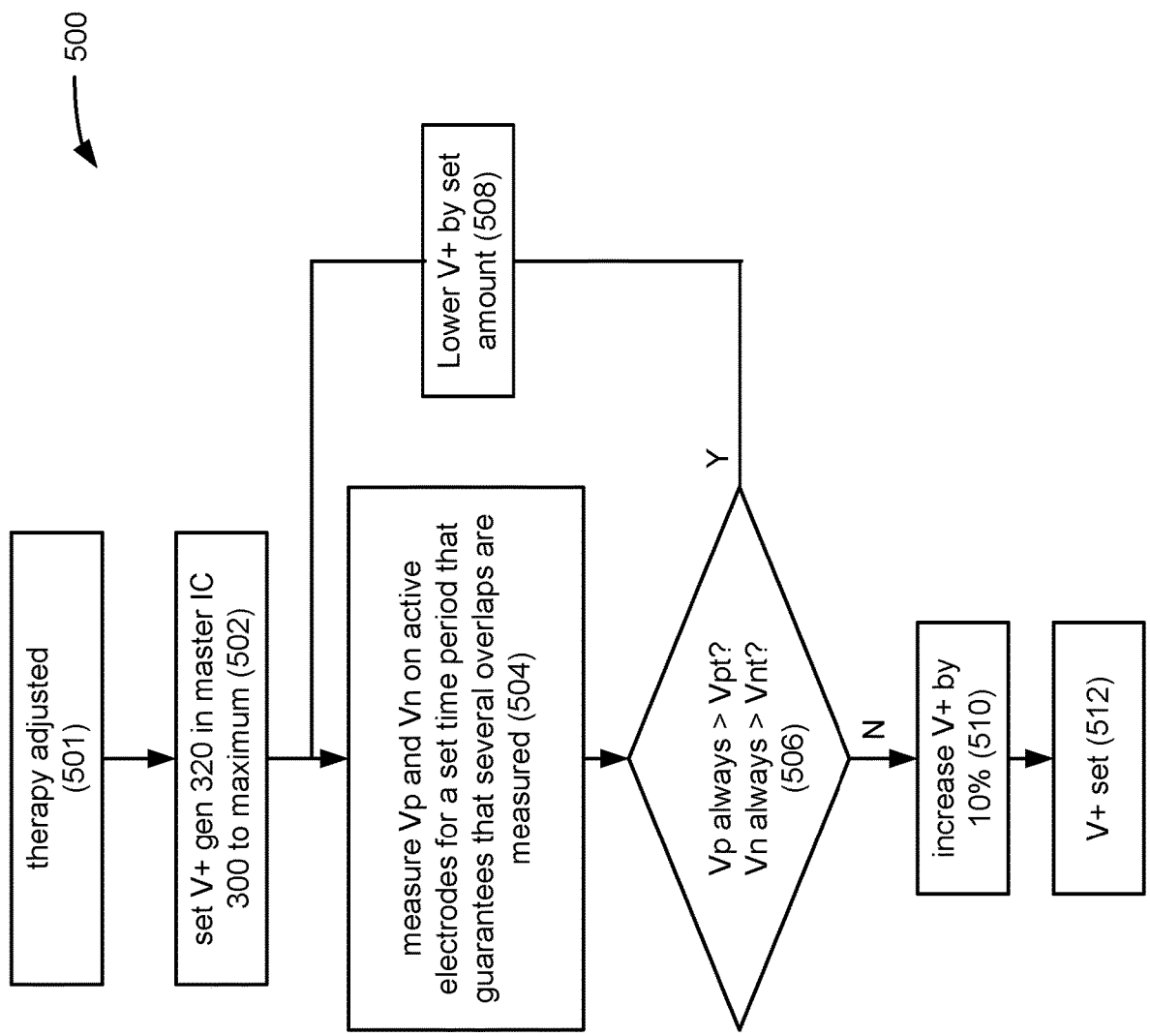

FIG. 6B describes one algorithm 500 for setting V+ to an optimal level in the improved system 290. The algorithm can start (501) at any time the IPG is operating and providing pulses, but in one example starts when therapy setting have been adjusted in some fashion. This can occur, for example, when the patient or clinician has used an external controller to change the frequencies, durations, or amplitudes of the pulses, or has chosen new electrodes for stimulation.

Once therapy has been adjusted and the algorithm starts, V+ can be set to a maximum voltage by the V+ generator 320 (502). This may be a value or about 18V or so. As will be seen, the goal in subsequent steps will generally be to lower V+ from this maximum voltage to a voltage that is closer to a threshold where V+ is too low to provide adequate power.

With V+ set to its maximum, therapy proceeds as programmed, and Vp and Vn are measured on active electrodes as discussed above, and for a time period that guarantees that these measurements will measure at least several overlaps (504). This time period can be determined by the V+ algorithm 500 by reviewing the frequencies (f1, f2) and pulse widths (pw1; pw2) programmed into the timing channels 176. From these parameters, it is not difficult for the algorithm 500 to compute a reasonable set time period for use in step 504. For example, if f1 equals 100 Hz, and f2 equals 40 Hz, and assuming pulse widths of 2 ms, the pulses (if started simultaneously) would overlap at 50 ms intervals, or 20 times a second. This means, at best, that Vp and Vn (which can't be measured simultaneously) could each be measured during periods of overlap 10 times per second. Assume, as algorithm 500 might to allow for error, the possibility of only partial overlaps, or simply to guardband the process, that only one of these 10 measurements per second will actually be captured, i.e., that one Vp and Vn measurement per second will capture an overlap. This would mean that during a 30 second period that 30 Vp and Vn measurements will capture an overlap. This would be a sufficient number of Vp and Vn measurements under these facts, and hence 30 seconds could comprise the set time period at step 504. In fact, many more Vp and Vn measurements (including those not taken during periods of overlap) would be captured and logged at the microcontroller 305 for algorithm 500 review during this this time period. If necessary, and to reduce harmonics between the frequencies, the algorithm 500 could stagger the beginning of the pulses at different times during this set time period to randomize the measurements and improve the probably of overlap capture.

Once the Vp and Vn measurements have been taken over the set time period, the algorithm 500 can review all of the Vp and Vn measurements during that time period (which would include both overlapping and non-overlapping measurements) and assess whether they always exceed particular threshold, i.e., Vpt and Vnt (506). These thresholds Vpt and Vnt can be chosen based upon the circuitry used in the PDACs 83 and 83' and the NDACs 84 and 84'. For example, if the DACs comprise current mirrors as is typical, see U.S. Pat. No. 7,444,181, it would be known that the P-channel output transistors in the PDACs and the N-channel transistors in the NDACs would be in saturation—and thus providing a proper amount of current—if Vp and Vn exceed 1.5V and 1.2V respectively. In other words, Vpt=1.5V, Vnt=1.2V, and the assessment at step 506 can proceed on that basis. Note that the determination at step 506 would likely be governed by the Vp and Vn measurements taken during the overlap periods, when such parameters would likely be at their lowest values due to the additional loading of V+ that overlapping provides.

Assuming that all Vp measurements exceed 1.5V, and all Vn measurements exceed 1.2V, the V+ algorithm 500 can conclude that V+ can possibly be lowered. This occurs at step 508, where V+ might be reduced from its maximum by some set amount, e.g., 1V, to 17V.

The Vp and Vn measurement process at step 504 can thus begin again at this new, reduced compliance voltage, and once again for the set time period determined earlier. Again, the Vp and Vn over this new time period can be assessed (506), and such measurements should generally be lower than occurred in the previous time period when V+ was higher.

Eventually, as V+ continues dropping, the measured Vp or Vn values will start to drop below their thresholds Vpt or Vnt, and again the first values to so fall would likely be those occurring during overlaps. This indicates that the compliance voltage V+ is now too low to provide the currents required, or at least (depending of the guardband built into the thresholds) that V+ is approaching this point. The process proceeds to step 510, where V+ is increased by some amount, e.g., 10% (510), and is set (512). Increasing V+ at this step 510 is desired to ensure that V+ is sufficiently high, and to mitigate concerns that conditions might change (e.g., electrode array movement, tissue changes, etc.) such that higher V+ values might be needed in the future for the particular therapy settings. If therapy settings are once again changed (501), the algorithm 500 can repeat to set a new value for V+.

While it is important to setting the compliance voltage to assess both overlapping and non-overlapping periods, the worst case scenario will not always occur during periods of overlap. This would be especially true if during an overlap a particular electrode is being called upon to act as both an anode and a cathode. For example, if Ec is programmed as the cathode and E1 as the anode in the master IC, but Ec is programmed as the anode and E7 as the cathode in the slave IC, overlapping of pulses would cause Ec to both source and sink current, and hence the amplitude of the current at that node would be subtracted (i.e., the addition of a positive and negative current). This could mean that power requirements during overlap would be less than when either IC issues pulses without overlap, and thus the worst case demanding the highest V+ would occur during periods of no overlap. In any event, because the V+ algorithm 500 monitors both overlapping and non-overlapping cases, the worst case scenario will be assessed and V+ set accordingly.

Although largely ignored for simplicity to this point, the timing channels used to define the interleaved pulses at the other side of the brain ($176_3$, $176_4$, $176_3'$, $176_4'$ in FIG. 5A) also require due consideration in an actual implementation in light of the concepts discussed herein. Thus, recovery switches 86 in the master IC 300 should be opened when either of active timing channels $176_2'$ or $176_4'$ are issuing pulses in the slave IC 300' so as not to short those pulses to Vbat. Likewise, recovery switches 86' in the slave IC 300' should be opened when either of active timing channels $176_1$ or $176_3$ are issuing pulses in the master IC 300. Similarly, during operation of the V+ algorithm 500, Vp and Vn measurements should be taken during overlapping and non-overlapping pulses issued by active timing channels $176_3$ and $176_4'$.

Although this disclosure has focused on a particular implementation of an IPG directed to providing DBS therapy at two different frequencies, it should not be understood as limited thereto. Many variations are possible. For example, the disclosed circuitry can support the issuance of cathodic and anodic pulses on any of the electrodes, and the case electrode need not act as the anode or, in bipolar simulation cases, need not even be used. Moreover, the disclosed circuitry can support the issuance of biphasic pulses, in which an anodic pulse at a particular electrode is followed by a cathodic pulse and vice versa. Moreover, while the disclosed dual-electrode driver IC system is particularly useful in issuing pulses of a first frequency from one of the ICs and pulses of another frequency from another IC, it need not be so limited. Both ICs can issue pulses of the same frequency, or can even issue aperiodic or random pulses depending on how it is programmed. The timing channels do not need to be dedicated to particular arrays, particular electrodes, or regions of the tissue being stimulated. Also, the disclosed approach is expandable to accompanying even further numbers of electrode driver ICs. For example, three or more IC could be used, with their electrode outputs shorted together, thus providing the ability to provide overlapping pulses of three or more different frequencies. Finally, the disclosed architecture need not be limited to DBS therapy, and can be applied to stimulation for a wide variety of therapies, such as those mentioned earlier.

Although disclosed as implemented in separate integrated circuits, the disclosed circuitry and methods can be employed in a single integrated circuit comprising both stimulation circuits 175 and 175', or can be employed with discrete circuits.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A stimulator device, comprising:
a plurality of electrode nodes and a plurality of electrodes configured to contact a patient's tissue, wherein each electrode node is coupled to a different one of the electrodes;
first stimulation circuitry configurable by a first timing channel dedicated to the first stimulation circuitry to provide first stimulation pulses to any of the electrode nodes; and
second stimulation circuitry configurable by a second timing channel dedicated to the second stimulation circuitry to provide second stimulation pulses to any of the electrode nodes;
wherein the first stimulation circuitry is configured by the first timing channel to cause a first current to flow through the patient's tissue by simultaneously applying the first stimulation pulses with opposite polarities at selected first of the electrode nodes; and
wherein the second stimulation circuitry is configured by the second timing channel to cause a second current to flow through the patient's tissue by simultaneously applying the first stimulation pulses with opposite polarities at selected second of the electrode nodes.

2. The device of claim 1, further comprising a case, wherein the first and second stimulation circuitries are within the case.

3. The device of claim 2, wherein one of the electrodes comprises a case electrode associated with the case.

4. The device of claim 3, wherein the case is conductive, and wherein the case electrode comprises the case.

5. The device of claim 1, wherein at least one of the selected first of the electrode nodes and at least one of the selected second of the electrode nodes comprise a common electrode node.

6. The device of claim 1, further comprising a first integrated circuit and a second integrated circuit, wherein the first stimulation circuitry is formed in the first integrated circuit, and the second stimulation circuitry is formed in the second integrated circuit.

7. The device of claim 1, wherein the first and second stimulation pulses respectively comprise first and second constant current pulses.

8. The device of claim 1, wherein the first stimulation circuitry is configured to provide the first stimulation pulses at a first frequency, and wherein the second stimulation circuitry is configured to provide the second stimulation pulses at a second frequency.

9. The device of claim 1, further comprising a microcontroller, and wherein the microcontroller, the first stimulation circuitry, and the second stimulation circuitry communicate by a bus in accordance with a bus protocol.

10. The device of claim 9, further comprising an integrated circuit, wherein the first stimulation circuitry and the second stimulation circuitry are formed in the integrated circuit.

11. The device of claim 10, wherein the first stimulation circuitry, the second stimulation circuitry, and the microcontroller are formed in the integrated circuit.

12. The device of claim 1, further comprising at least one electrode array, wherein the electrode array comprises the plurality of the electrodes.

13. The device of claim 12, wherein the at least one electrode array is configured for implantation in a patient's brain.

14. The device of claim 1, wherein the electrode nodes are each coupled to the different one of the electrodes by capacitors.

15. The device of claim 1, wherein the device comprises an implantable stimulator device.

* * * * *